US00PP37472P2

(12) United States Plant Patent
Nannes

(10) Patent No.: US PP37,472 P2
(45) Date of Patent: Jun. 16, 2026

(54) ***ECHEVERIA* PLANT NAMED 'BINL-77120280'**

(50) Latin Name: ***Echeveria* spp.**
Varietal Denomination: BINL-77120280

(71) Applicant: Botanical Innovation B.V., Wageningen (NL)

(72) Inventor: Jacobus A.M. Nannes, Nairobi (KE)

(73) Assignee: Botanical Innovation B.V.

( * ) Notice: Subject to any disclaimer, the term of this patent is extended or adjusted under 35 U.S.C. 154(b) by 0 days.

(21) Appl. No.: 19/344,883

(22) Filed: Sep. 30, 2025

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP34,522 P2 * 8/2022 van Langen ..... Plt./373

* cited by examiner

*Primary Examiner* — Susan Mccormick Ewoldt
*Assistant Examiner* — Zachariah Allan Kay

(57) ABSTRACT

A new and distinct cultivar of *Echeveria* plant named 'BINL-77120280' is disclosed, characterized by flattened rosettes with intense purple color on the leaf ends, having a whitewash look. The new cultivar is an *Echeveria*, typically used as an ornamental plant.

2 Drawing Sheets

Figure 1:
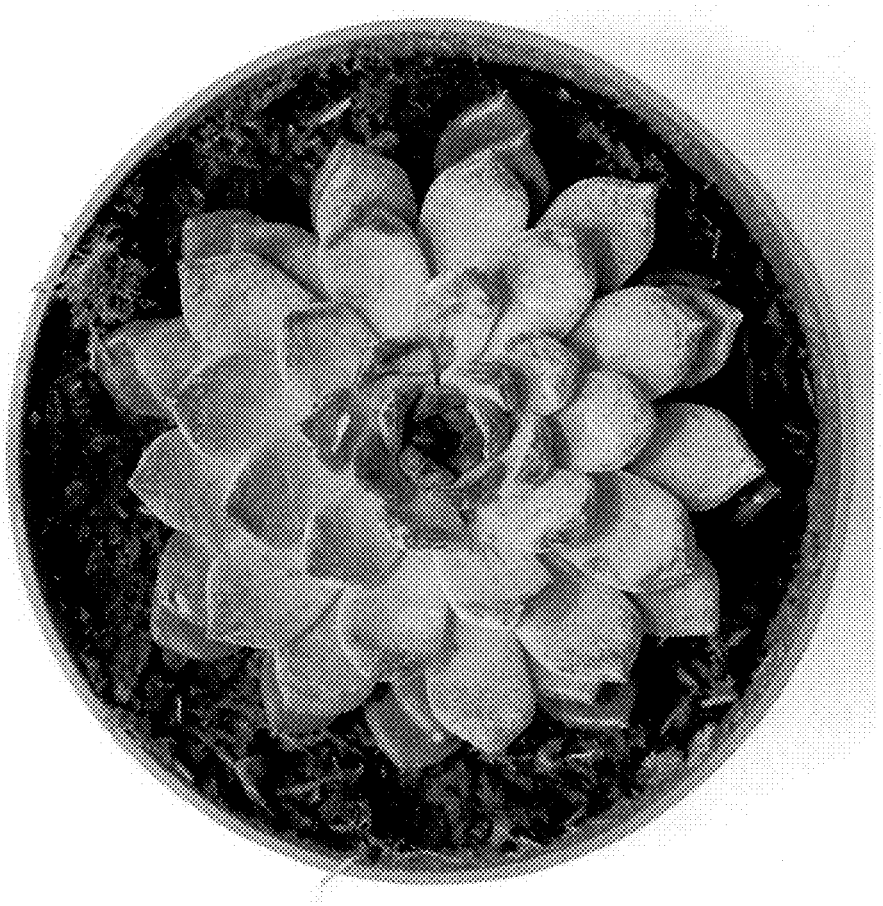

Latin name of the genus and species: *Echeveria* spp.
Cultivar denomination: 'BINL-77120280'.

BACKGROUND OF THE INVENTION

The new cultivar is a product of a planned breeding program to produce distinct and better performing *Echeveria* cultivars. The new cultivar is the result of a crossing made by the inventor in May of 2020. The seed parent is the unpatented *Echeveria* 'Silver Shine'. The pollen parent is the unpatented *Echeveria* 'Black Prince'. The new cultivar was selected by the inventor in August of 2021 at a nursery in Nairobi, Kenya.

Asexual reproduction of the new cultivar 'BINL-77120280' by terminal cuttings was first performed at the same nursery in Nairobi, Kenya in August of 2021, and has shown that the unique features of this cultivar are stable and reproduced true to type through successive generations.

SUMMARY OF THE INVENTION

The cultivar 'BINL-77120280' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BINL-77120280'. These characteristics in combination distinguish 'BINL-77120280' as a new and distinct *Echeveria* cultivar:

1. Intense purple color of the leaf-ends, having a white-washed/glaucous look.
2. Thick leaves, hence not stretching easily or quickly.
3. Nice rosette-like plant-shape.

PARENT COMPARISONS

Plants of the new cultivar 'BINL-77120280' are similar to plants of the female parent in most horticultural characteristics, however, plants of the new cultivar 'BINL-77120280' differ from in the following characteristics:

1. Leaf color of the new cultivar is pale-yellow at the base, turning into an intense purple color on the leaf-ends, having a whitewash/glaucous look. Leaf color of the seed parent is evenly grey-pink, also having a white-wash look.
2. Plants of the new cultivar have a flat growth habit, while plants of the seed parent have a more upright growth habit.

Plants of the new cultivar 'BINL-77120280' are similar to plants of the male parent in most horticultural characteristics, however, plants of the new cultivar 'BINL-77120280' differ in the following characteristics:

1. Leaf color of the new cultivar is pale-yellow at the base, turning into an intense purple color on the leaf-ends, having a whitewash/glaucous look. Leaf color of the pollen parent is evenly dark purple-black.
2. Plants of the new cultivar have a whitewash look, while plants of the pollen parent do not have a whitewash look.

COMMERCIAL COMPARISONS

Plants of the new cultivar 'BINL-77120280' are similar to plants of the commercial cultivar *Echeveria* 'Morning Dew', unpatented. However, plants of the new cultivar differ in the following characteristics:

1. Leaf color of the new cultivar is pale-yellow at the base, turning into an intense purple color on the leaf-ends, having a whitewash/glaucous look. Leaf color of this comparator is blueish green with pinkish-red leaf-tips, also having a whitewash look.

2. Plants of the new cultivar have a flat growth habit, while plants of this comparator have a more upright growth habit.

Plants of the new cultivar 'BINL-77120280' are similar to plants of the commercial cultivar *Echeveria* 'Blue Speed', unpatented. However, plants of the new cultivar differ in the following characteristics:

1. Leaf color of the new cultivar is pale-yellow at the base, turning into an intense purple color on the leaf-ends, having a whitewash/glaucous look. Leaf color of this comparator is blueish green, maturing to light green.
2. Leaves of the new cultivar are less pointed than leaves of this comparator.

BRIEF DESCRIPTION OF THE PHOTOGRAPHS

The accompanying photograph in FIG. 1 illustrates in full color a top-down view of a typical plant of 'BINL-77120280' grown in a greenhouse. The plant is approximately 24 weeks of age.

Figure 2:
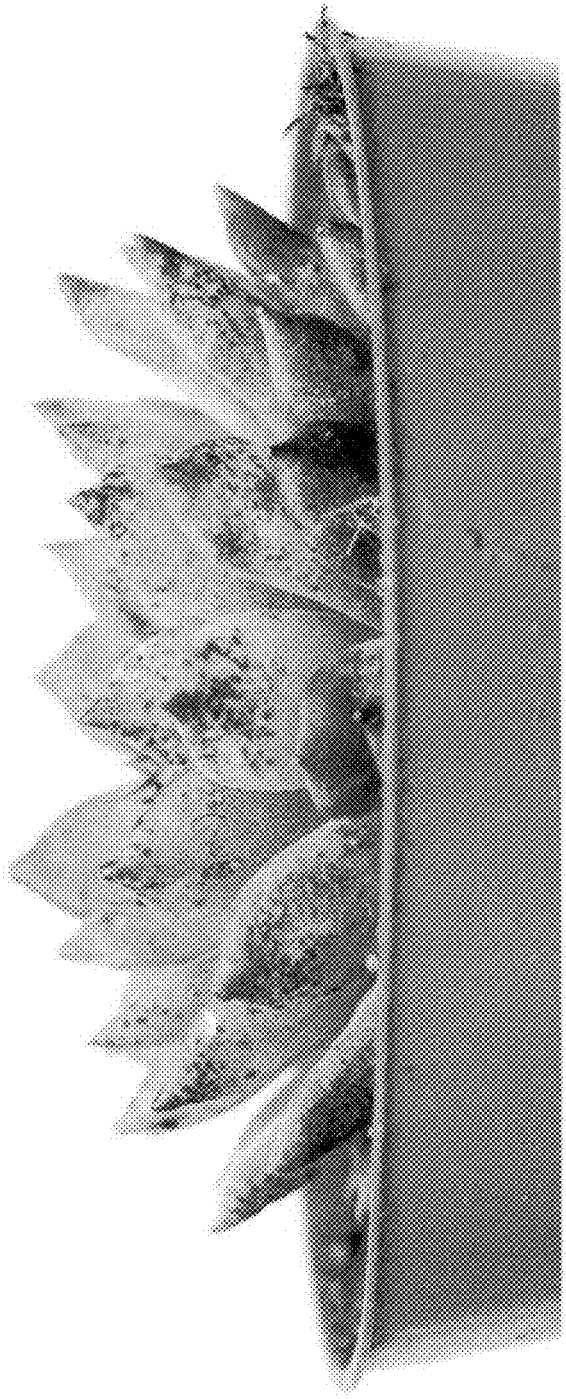

FIG. 2 is a side-view of the same plant.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'BINL-77120280' plants at 24 weeks of age, grown in a greenhouse in Nairobi, Kenya during August. The growing temperature ranged from 12° C. to 20° C. at night to 20° C. to 28° C. during the day. Measurements and numerical values represent averages of typical flowering types.

Botanical classification: *Echeveria* spp. 'BINL-77120280'.

PROPAGATION

Time to initiate roots: About 14 days in summer, 21 days in winter at approximately 20° C.

Time to produce rooted cutting: About 45 days in summer, 60 days in winter at approximately 20° C.

Description of roots: Thin, herbaceous, moderately dense, freely branching. White in color, not accurately measured with R.H.S. chart.

PLANT

Plant type: Tender succulent perennial.

Plant shape: Flattened (basal rosette).

Growth habit: Basal rosette of leaves.

Plant spread: Average 10.7 cm.

Height: Average 4.1 cm.

Age of plant described: Approximately 24 weeks.

Branching habit: Leaves in basal rosettes, no main stems or lateral stems present.

Pinching: Pinching not required.

FOLIAGE

Leaf:

*Arrangement*.—Single rosette.

*Quantity*.—Average 60 per rosette.

*Average length*.—4.8 cm.

*Average width*.—1.6 cm.

*Shape*.—Oblong-obovate.

*Aspect*.—Very slightly concave, leaves in an average angle of 40° to horizontal (=0°).

*Apex*.—Short apiculate. Base: Cuneate.

*Margin*.—Entire.

*Texture*.—Top surface: Glabrous, smooth. Bottom surface: Glabrous, smooth.

*Pubescence*.—None; both sides glabrous.

*Luster, upper side*.—Moderately glossy, but covered with a thin waxy layer, colored RHS Greyed-Purple N187C.

*Luster, under side*.—Moderately glossy, but covered with a thin waxy layer, colored RHS Greyed-Purple N187C.

*Rugosity, upper side*.—Non-rugose.

*Rugosity, under side*.—Non-rugose.

*Color*.—Young foliage upper side: A blend of RHS Greyed-Purple N186C and N187A, narrowly edged Greyed-Purple 187C, leaf fading brown to black towards the top; a blend of Brown 200A and Black 203C, and leaf fading to Yellow-Green 150D towards the base. Young foliage under side: RHS Greyed-Purple N186C, narrowly edged Greyed-Purple 187C, leaf fading brown to black towards the top; a blend of Brown 200A and Black 203B, leaf fading to Purple 75D towards the base. Mature foliage upper side: A blend of RHS Yellow-Green 146D and 147C, upper half strongly tinged and finely blotched Greyed-Purple 183C, tipped Brown 200A. Mature foliage under side: RHS Yellow-Green 148C, upper half strongly tinged and finely blotched Greyed-Purple 183D, fading to Greyed-Purple N186C to Brown 200A towards the top.

*Venation*.—Pattern: No veins visible.

*Other*.—Leaves succulent, average thickness: 6 mm.

OTHER CHARACTERISTICS

Flower: Not observed to date.

Seeds and fruits: None observed to date.

Disease/pest resistance: Neither resistance nor susceptibility to normal diseases and pests of *Echeveria* has been observed.

Temperature tolerance: Tolerates temperatures up to 40° C. Hardy to USDA zones 10 to 12.

Moderate tolerance to rain. High tolerance to wind.

What is claimed is:

1. A new and distinct cultivar of *Echeveria* plant named 'BINL-77120280' as herein illustrated and described.

* * * * *